US005853726A

United States Patent [19]

Chevereau

[11] Patent Number: 5,853,726

[45] Date of Patent: Dec. 29, 1998

[54] METHOD FOR EXTRACTING AND FIXING AROMAS ON NON-AQUEOUS SUBSTRATE, MACHINE FOR IMPLEMENTING THE METHOD, AND PRODUCT THEREBY

[76] Inventor: Pierre Chevereau, 1, avenue Naast, 94340 Joinville le Pont, France

[21] Appl. No.: 504,859

[22] Filed: Jul. 21, 1995

[51] Int. Cl.$^{6}$ .............................. A61K 35/78; A61K 7/46

[52] U.S. Cl. .................................... 424/195.1; 204/158.2; 512/1; 426/241

[58] Field of Search ...................... 424/195.1; 204/158.2; 512/1; 252/522; 426/241

[56] References Cited

U.S. PATENT DOCUMENTS

| | | | |
|---|---|---|---|
| 4,556,575 | 12/1985 | Katz et al. | 426/594 |
| 5,002,784 | 3/1991 | Pare et al. | 426/241 |
| 5,338,557 | 8/1994 | Pare | 426/241 |
| 5,434,122 | 7/1995 | Lorina et al. | 504/118 |
| 5,458,897 | 10/1995 | Pare | 426/241 |

FOREIGN PATENT DOCUMENTS

| | | |
|---|---|---|
| 2055390 | 5/1992 | Canada . |
| 398798 | 11/1990 | European Pat. Off. . |
| 485668 | 5/1992 | European Pat. Off. . |
| 969905 | 12/1950 | France . |

*Primary Examiner*—Leon B. Lankford, Jr.
*Assistant Examiner*—Christopher R. Tate
*Attorney, Agent, or Firm*—Fulbright & Jaworski L.L.P.

[57] ABSTRACT

A process for extraction and fixation of aromas on a non-aqueous substrate, according to which aromatic plants, seeds, or fruits and a substrate such as a fat or oil are placed in a treatment zone and microwave radiation is produced in the treatment zone so as to heat primarily the aqueous parts of the plants rather than the components of the substrate, a machine to implement the process of the invention which comprises primarily a treatment vessel and a microwave radiation apparatus, and a product obtained by said process.

6 Claims, 3 Drawing Sheets

METHOD FOR EXTRACTING AND FIXING AROMAS ON NON-AQUEOUS SUBSTRATE, MACHINE FOR IMPLEMENTING THE METHOD, AND PRODUCT THEREBY

BACKGROUND OF THE INVENTION

The present invention concerns a process of extraction and fixation of aromas on a non-aqueous substrate. It also concerns a machine to implement the process and a product obtained according to the process.

The invention is applicable in the industry of culinary and cosmetic preparations.

In the prior art, process have already been proposed which enable extraction of aromas contained in plants, followed by their fixation on an oil or a fat, principally by maceration in a liquid. However, such a process does not enable efficient transfer of the aromas into the maceration liquid and demands a great deal of time.

In particular, it is known to produce oils perfumed by additives of perfumes or of plants with various aromas such as: basil, thyme, or parsley in the case of seasoning oils, but also with other plants whose aromas are valued in the fabrication of cosmetics.

To increase the efficiency of maceration, heating the preparation has already been proposed. This has, within certain limits, the effect of increasing the efficiency of the extraction of the aroma and its transfer onto the oil, but it degrades the perfume of aromatic plants.

One object of the invention is to enable extraction and transfer of aromas from a plant to a substrate such as an oil with improved efficiency and with reduced treatment times while retaining the quality and the purity of the perfumes.

Another object of the process of the invention is to avoid the decomposition or, at the very least, the denaturing of the substrate such as an oil.

In the prior art, it has also been proposed to accelerate and to improve the capacity of treatment of processes using organic extractants by differentially heating a biological material from which one wishes to extract volatile oils. Heating is provided by microwave radiation and extraction is provided by extractants selected among the organic solvents of the aliphatic type. Such prior art is represented in particular by:

CA-A-2,055,390

EP-A-0,398,798

EP-A-0,485,668.

However, the extractant is mixed with the extracted volatile oils, and it is also necessary to ensure the removal of the extractant, which is often toxic, and the fixation of the aromas on a substrate so as to produce a useable final material.

It is a further object of the invention to propose a novel, advantageous process whereby the product obtained presents a real advance compared to the products obtained according to previous processes.

SUMMARY OF THE INVENTION

In effect, the invention concerns a process for extraction and fixation of aromas on a non-aqueous substrate, according to which aromatic plants, seeds, or fruits and a substrate such as a fat or oil are placed in a treatment zone and, finally, microwave radiation is produced in the treatment zone so as to heat primarily the aqueous parts of the plants rather than the components of the substrate.

The invention also concerns a machine to implement the process of the invention which comprises primarily a treatment vessel and a microwave radiation apparatus.

According to one aspect of the invention, a microwave radiation apparatus is controlled by a control circuit which enables regulating exposure as a function of the temperature measured by a sensor and exposure duration measured by a timer, with the control circuit regulating the radiation apparatus as a function of pre-entered characteristics.

The invention also concerns a aromatized oil as a product obtained by the process.

BRIEF DESCRIPTION OF THE DRAWINGS

Other characteristics and advantages of the present invention will be better understood with the help of the description and drawings which are

DETAILED DESCRIPTION OF THE INVENTION

One execution of the process according to the invention, which uses a machine suited to produce a perfumed oil according to the process of the invention, will be described as an illustrative example.

Figure 1:
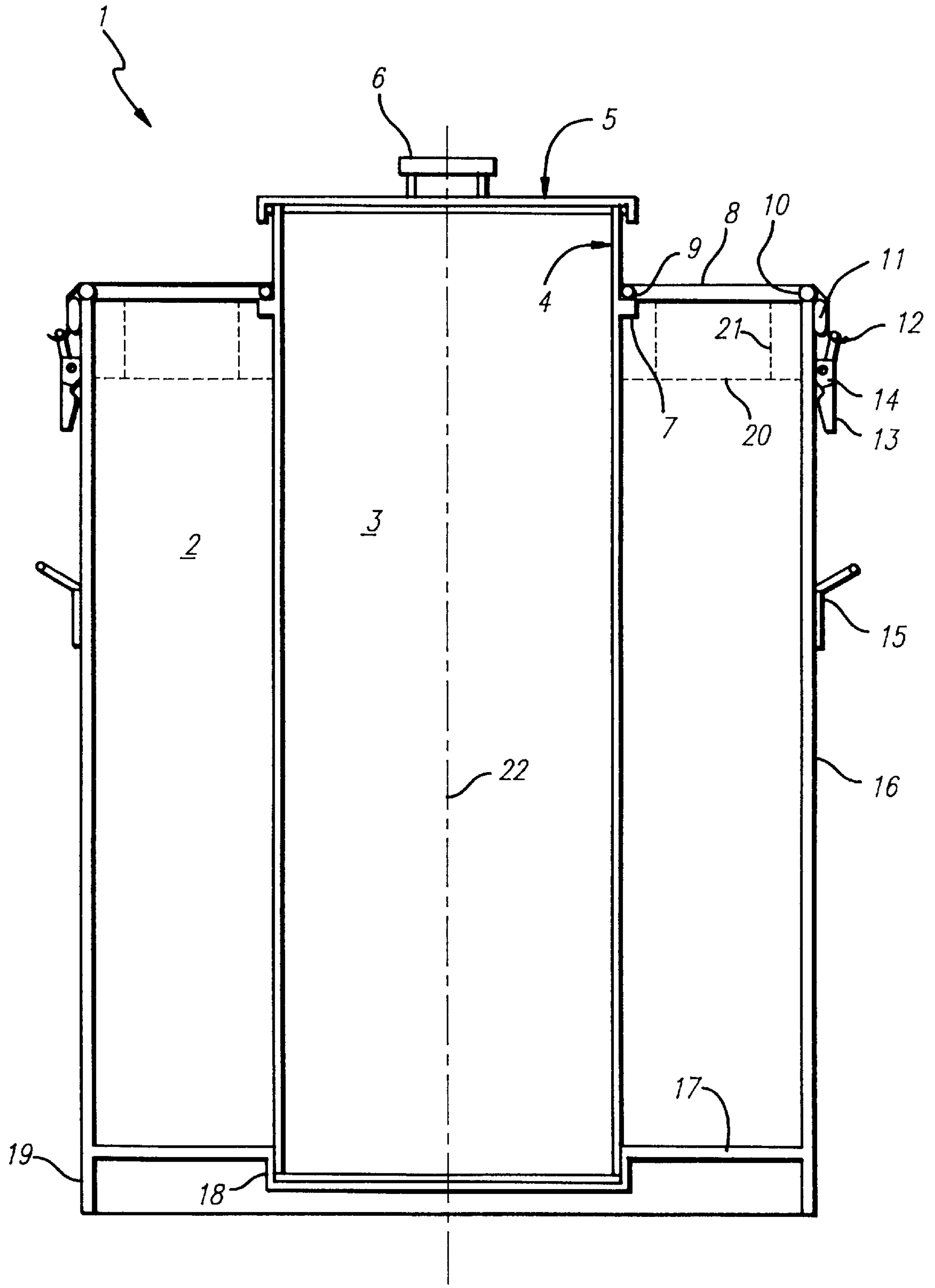
FIG. 1: a schematic of an embodiment of a treatment vessel according to the invention.

An operator uses at least one treatment vessel depicted in FIG. 1. This vessel 1 includes an essentially cylindrical outer body 16 made of mechanically resistant material. The outer wall 16 is also made of a material opaque to the microwave radiation which will be applied later in the process.

A cylindrical tube 4 with an axis 22 is placed in a recess 18 in the bottom 17 of the outer body 16. The outer body 16 is also provided with a footed base 19 enabling its placement on other apparatuses or on a support. The cylindrical tube 4 may have a plug on its bottom. It [the tube 4] is made of a plastic material such as Altuglass, transparent to the microwave radiation which will be applied later at the time of the process.

Two zones have also been delimited in the treatment vessel 1:

- a first zone 2 called a treatment zone whose upper level is bounded by a screen 20 attached by tabs 21 to a first cover 8 so as to ensure a safety space;
- a second zone 3 designed to later accommodate a radiation apparatus, depicted in FIG. 2, and closed by a second cover 5 provided with a locking and gripping means 6 such as a handle.

The outer body 16 is also provided with gripping means 15 such as handles which enable its manipulation at the time of harvesting of the plants and at the time of the execution of the treatment operations.

The tube 4 has an annular flange 7 designed to accommodate an O-ring 9 bonded on the bottom of the first cover 8 so as to constitute a leakproof seal between the first cover 8 and the tube 4.

The first cover 8 also has a bonded O-ring 10 which is supported on the upper edge of the outer body 16 so as to constitute a leakproof seal.

The first cover 8, which has a central bore to allow the top of the tube 4, which is taller than the outer body 16, to extend beyond it, also includes anchoring rims 11 on which hooks 12 of a hinged latch consisting of a lever 13 turning on a base 14 made in one piece with the outer body 16 are placed.

The cut plants are first placed in the treatment vessel 1; then, a quantity of a substrate such as an oil is poured in such that the aromatic plants soak in it. The aromatic plants contain aqueous components which are the carrier for the perfumes to be extracted and to be fixed on the substrate, by heating them rather than the components of the substrate (or oil).

Next, the treatment zone 2 of the vessel 1 is exposed to microwaves produced by emitters integrated into a radiation apparatus and which are directed toward the interior of the vessel.

In one embodiment, a means of focusing the microwaves is disposed to focus the radiation as much as possible on the interior zone of the vessel where the plants are disposed.

The microwave radiation emitters are then powered and regulated so as to produce a quantity of heat sufficient to heat the submerged plants without degrading the perfumes. In one exemplary embodiment, the best results were obtained with an exposure of 4 to 6 minutes.

More generally, it has been discovered that the best results were obtained when the external temperature of the treatment vessel was slightly less than 50° C. at the end of exposure. Under these conditions, the ratio of the temperatures of the plants and of the oil is in the proportion of 1 for the oil and 2 for the plants. When 40° C. is reached in the oil, the plants in its structure are at 80° C. It is thus possible to collect the perfumes most consistently, since the temperatures are low enough for the aromatic products to be volatilized without being altered.

The machine according to the invention is thus provided with microwave radiation emitters powered via a circuit controlling the power and/or the duration of exposure (i.e., a “controller”), according to either a predetermined algorithm or “real time” adjustments by a human operator.

The control circuit is connected by means of a suitable interface to a sensor for the external temperature of the vessel as well as to an exposure timer.

The maximum exposure duration (6 minutes) is entered on the timer, while a maximum admissible external temperature (50° C.) is entered for control.

In numerous applications, it was noted that the microwave exposure was sufficient when bubbles come out of the plant parts.

For that purpose, it is possible to dispose a manual switch enabling an operator to interrupt the emission of the microwaves. In a variant, the machine of the invention includes an automatic means of detection of the appearance of bubbles on the plant parts. Such a means may consist of a means of detection of acoustic emissions disposed in the liquid or on the wall of the vessel. The acoustic emission detection signal is then compared in frequency and/or in intensity to a threshold detection signal.

In a variant, the bubbles are detected by a means of measurement of the gas pressure in the top of the treatment vessel 1, with this being sealed.

In another valiant, the safety space in the treatment zone 2, between the screen 20 and the first cover 8, which is subjected to an increase in pressure by the release of aromatic vapors, is provided with an overpressure reduction means. Such a means may include an expansion tank or an annexed circuit with a low-temperature condensation unit to recover the volatilized essence on the surface.

After the process according to the invention, the vessel cools slowly. A slight increase was noted in the external temperature due to the evacuation of the amount of heat absorbed in the plant parts, which leads to the question of whether the admissible external temperature selected to interrupt the microwave exposure of the treatment vessel should be selected in consideration of the final release of heat in order to remain below the denaturation point of the substrate (olive oil in the exemplary embodiment).

In a preferred embodiment, the treatment vessel is provided with a cooling means. In the configuration of FIG. 1, cooling takes place in the upper part of the treatment vessel 1, either by circulating a cooling fluid in a suitable exchanger or by spraying cold water on the upper external parts of the vessel. Of course, any number of cooling mechanisms, such as heat exchange, may be employed.

In one embodiment, the means of cooling by spraying consists of at least one spray nozzle for a cooling liquid such as water.

Figure 2:
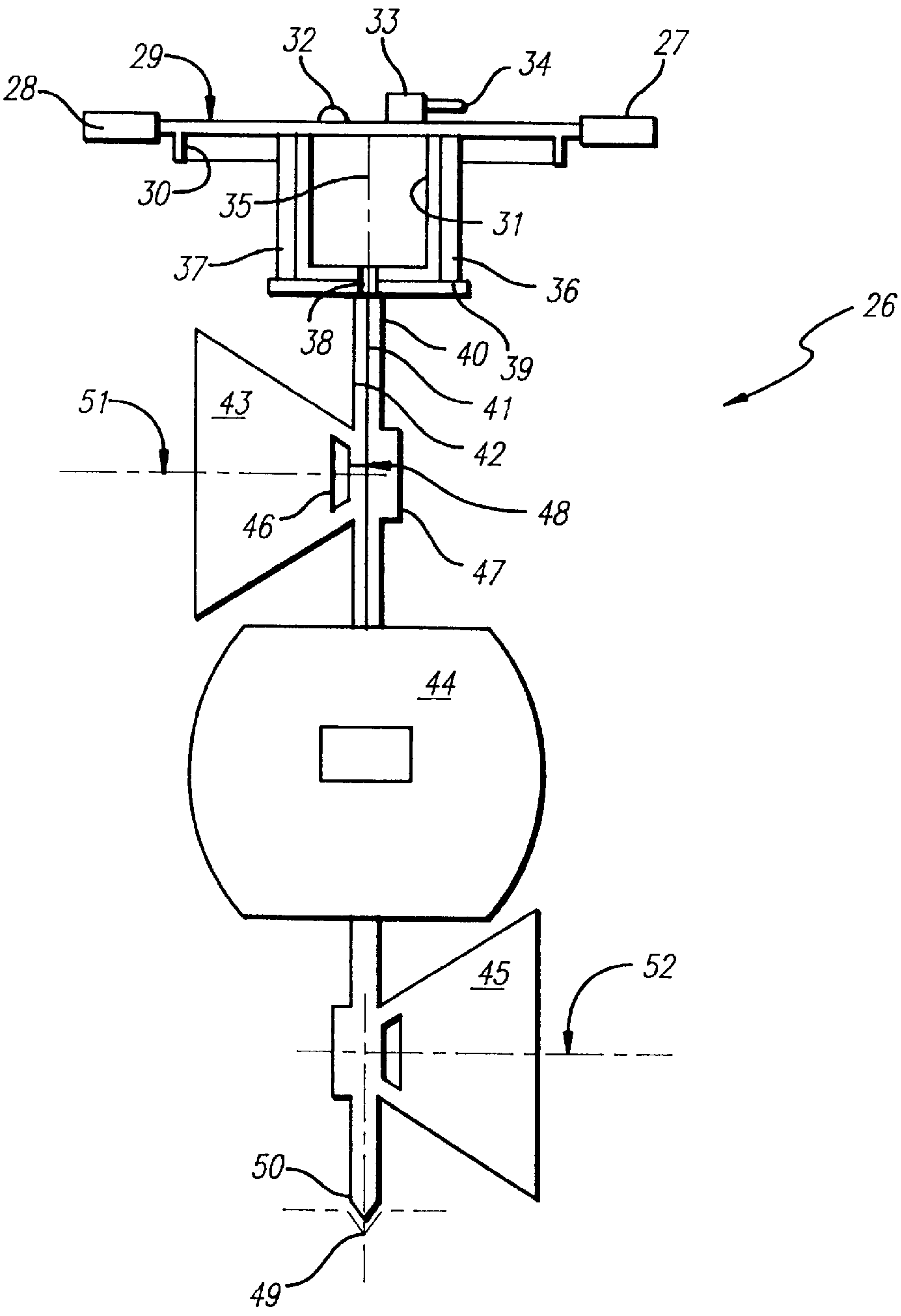
FIG. 2: a schematic of an embodiment of a radiation apparatus of the machine according to the invention.

FIG. 2 depicts an embodiment of a radiation apparatus suited to the treatment vessel 1 of FIG. 1.

The operator fills the treatment zone 2 of the vessel 1 with plants of a specified type according to weights specified as a function of the quantity and the nature of the fat used. The screen serves to gently hold the plants in the substrate, to prevent their being burned by direct radiation.

The mixture is then cooled by spraying water or other coolant locally on the mixture, by heat exchange, or by other means known in the art.

He then fills the treatment zone 2 of the vessel 1 with the desired oil and introduces the radiation apparatus depicted in FIG. 2 into the radiation zone 3 of the vessel 1.

The radiation apparatus includes primarily a body 26 composed of a cylindrical rod 40 made of a plastic material which supports focused microwave emitters 43–45. Each focused emitter includes a commercially available microwave source, of radiated power on the order of 700 watts of electricity, and a focusing reflector which produces a beam of microwave radiation with the axis 51 for the focused emitter 43 (52 for emitter 45) with essentially parallel rays all perpendicular to the rod 40.

The rod 40 is in one piece with a disk 39 and with the shaft 38 of the rotor of an electric motor 31, whose axis 35 is aligned on that of the rod 40. With the radiation apparatus of FIG. 2 installed in the treatment zone 3 of the vessel 1 of FIG. 1, the axes 35 of the motor, of the rod 40, and the axis of the vessel 1 are merged. The end 50 of the rod 40 is provided with a centering means 50, in the form of a point, which enters a seat 49 in the bottom of the tube 4 of the vessel 1.

The motor 31 is attached by an attachment means such as screws 32 to a cover 29 of which the interior diameter of the flange 30 is identical to the external diameter of the tube 4 of the vessel 1 so as to substitute for the second cover 5 at the time of the radiation step, when the radiation apparatus is installed in its treatment zone.

The motor 31 is equipped with an electrical connector 33 from which a power cord 34 extends, linking it to a suitable electric power source. This source may consist of a generator set if the treatment is carried out at the site of the harvest of the aromatic plants.

For manipulation of the radiation apparatus, the cover 29 is provided with handles 27, 28.

In one embodiment, not depicted in the drawings, but directly comprehensible to the person skilled in the art with what follows, the base of the tube 4 is not closed and communicates with the exterior of the treatment vessel 1, with a means of leakproofing then preferentially provided between the base of the tube and the treatment zone 2. The top of the tube 4 then accommodates a treatment apparatus like the apparatus 26, but also including forced cooling means, in particular by ventilation. This is the case particularly if the microwave emitters are connected to high voltage power supplies including at least one high voltage transformer, as is usually the case. Then, the transformers are installed under the cover 29 and next connected to arrangements analogous to the brushholders 35 and 36 of FIG. 2, then via the rotating disk 39 to suitable lines to the emitters themselves.

Moreover, the motor 31 is mounted on the cover 29 on the outside of the vessel and its shaft 38, as in the embodiment of FIG. 2, is connected to the hollow rod 40 by one end, and, in this variant, is connected to a centrifugal ventilation turbine by the other end. The flow of air is forced by suitable inlets in the cover 29, then into the tube 4 so as to produce forced air flow on the high voltage transformers of which the primaries are connected to the connector 33 and the secondaries to the conducting lines of the rod 40, on the emitters in the tube 4, and on the internal walls of the tube 4, and it finally leaves through the open base of the tube 4.

Returning to FIG. 2, the microwave emitters 43–45 are powered with the help of the disk 39 which has two conducting tracks (not shown in the drawings) on its top surface which are electrically connected to two respective conductors 41, 42 which carry the electrical energy to suitable inputs of each of the microwave sources such as the source 46 which is connected in parallel to the conductors 41, 42.

The tracks of the disk 39 are in contact with brushes which slide into the bore of hollow tubes 36 and 37 and which are held against the conducting tracks by the action of springs (not shown) electrically connected to suitable polarities or phases of the electrical source via conducting wires connected to the connector 33.

In the arrangement according to FIG. 2, the three focused emitters 43–45 are vertically distributed along the rod 40 such that the radiation beams 51, 52 are virtually without discontinuity in the vertical direction. The central axes of these beams are distributed in the plane perpendicular to the axis of the rod 40 at 120° from each other. Thus, with the rod 40 rotating continuously, uniform radiation of the entire treatment zone 2 in the vessel 1 is obtained. The arrangement of the focusing means is also determined as a function of the power radiated and designed to limit the interference between beams.

In another arrangement of the focused emitters on the rod 40, the emitters are disposed two by two, head to foot, with the central axes of their beams aligned and their radiation opposed. In this manner, the density of radiation is increased in the treatment zone per unit of treatment height. It is possible to provide a plurality of pairs of emitters, head to foot, along the rod 40.

The microwave emitters 43–45 are attached by suitable attachment means, such as the means 47, on the rod 40, in particular by a flange made in one piece with the source 46 and the focusing reflector provided with a means of clamping around the rod. Moreover, the source 46 is electrically connected to the electric lines 41 and 42 by a suitable connection means 48.

The treatment is either controlled by the operator or with the help of the aforementioned controller.

In the process according to the invention, the cooling of the mixture is maintained for a period which depends on the physico-chemical characteristics of the substrate used (such as oil).

The cooling is maintained until the internal temperature of the vessel has dropped back down to between 40° and 45° C. However, if the radiation step is repeated several times, it is possible, to reduce the subsequent treatment times, to cool back to only between 42° and 48° C.

The treatment vessel is then emptied into a separation means enabling isolation of the aroma-laden substrate (such as perfumed oil) obtained according to the process of the invention from other substances, such as cooling water or water freed from the initial aromatic plants by the microwave treatment. By this step, voltalized essences are removed. One such separation means is made up of a vessel with a conical bottom.

Figure 3:
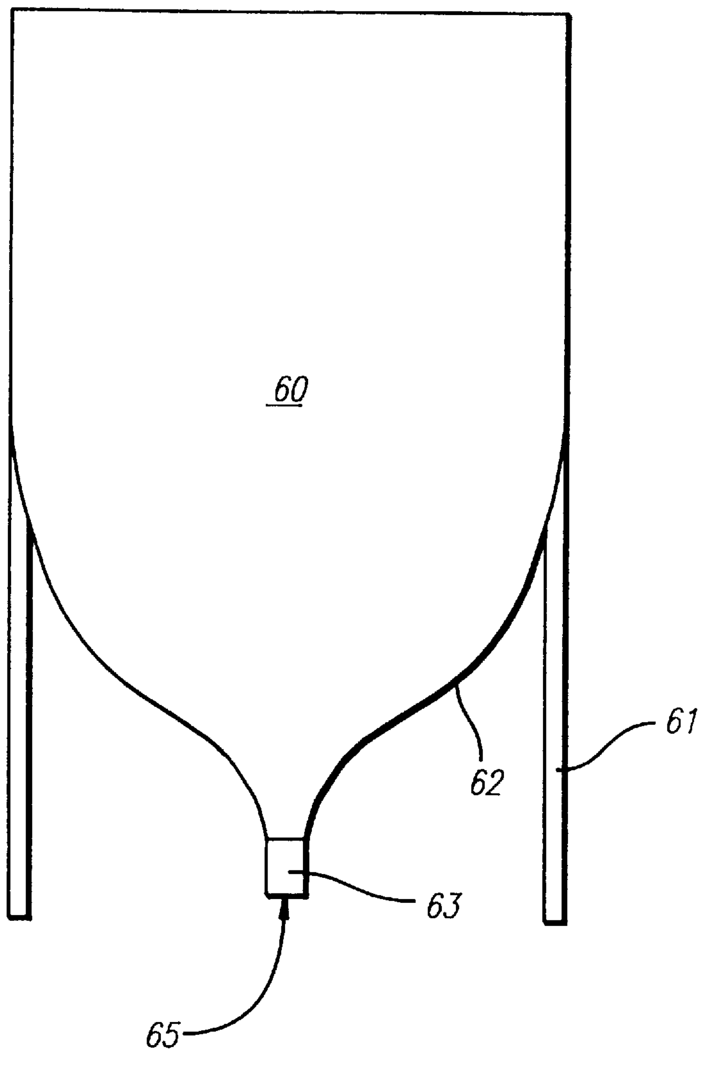
FIG. 3: an embodiment of a component of the machine according to the invention.

FIG. 3 depicts a vessel serving as a separation means in one embodiment.

The separation vessel includes a main body 60 through the top opening of which the oil is introduced from the treatment vessel, either by pouring from its own top opening or through an opening on its bottom closed by a valve.

The bottom of the separation vessel is formed into a conic shape 62 whose bottom 65 is opened by a needle valve 63. The separation vessel is mounted on legs 61 and is designed to receive, over a period of several hours, the charges of aromatized oil produced using the treatment vessel-radiation apparatus pairs. The bottom of the separation vessel is made of a transparent material or has an observation window to assess whether the bottom of the vessel is, in fact, free of oil. In this case, the valve 63 is used to evacuate the materials to a waste filtering unit. Then, the aromatized oil is evacuated to other treatment instruments and separated from materials and wastes, such as water.

In particular, the aromatized substrate (or aromatized oil) passes through a strainer to retain especially the plant parts, then through a clarification unit, before arriving in a storage and/or packaging unit.

In one embodiment of the invention, the microwave exposure is repeated after the temperature of the mixture has dropped below a certain threshold. In the exemplary embodiment, the re-exposure decision was made when the internal temperature reached 35° C.

In addition, to complete the process according to the invention, the plant parts removed from the strainer are placed in the press or in the centrifuge associated with the machine according to the invention, so as to recover the substrate (oil) which adheres thereto.

The process according to the invention is not exclusive of other treatment processes with which it is advantageously combined.

I claim:

1. A process of extraction and fixation of aromas on a non-aqueous substrate, whereby aromatic plants and a non-aqueous substrate selected from the group consisting essentially of fats and oils are disposed in a treatment zone and, finally, microwave radiation is produced in the treatment zone so as to heat primarily the aqueous parts of the plants rather than the components of the substrate, wherein:

the plants are completely submerged in the substrate;

the microwave radiations are regulated so as to produce a quantity of heat sufficient to heat the submerged plants without decomposing the substrate with temperatures are sufficiently low such that the aromatic products are volatilized without being altered, by one or more of the following:

with an exposure of 4 to 6 minutes, or by stopping the exposure when the external temperature of the treatment vessel is still lower than 50° C., or when the ratio of the temperatures, measured in degrees centigrade, of the plants to the substrate is approximately two to one; or the treatment is interrupted upon the appearance of bubbles in the mixture;

the process comprises a step of local cooling by exchange or by spraying;

the process comprises a step of recovery of the volatilized essences;

the process comprises a separation step, then a clarification step, and finally a storage or packaging step;

the radiation step is repeated a plurality of times, separated by cooling steps; and a resulting end product consists of an aromatized substrate.

2. The process of claim 1 wherein the step of regulating microwave radiations comprises producing a sufficient quantity of heat with an exposure of 4 to 6 minutes.

3. The process of claim 1 wherein the step of regulating microwave radiations comprises stopping exposure when the external temperature of the treatment vessel is still lower than 50° C.

4. The process of claim 1 wherein the step of regulating microwave radiations comprises stopping exposure when the ratio of the temperatures, measured in degrees centigrade, of the plants to the substrate is approximately two to one.

5. The process of claim 1 wherein the step of regulating microwaves radiations comprises interrupting the treatment upon the appearance of bubbles in the mixture.

6. A microwave radiation apparatus for performing the process of extraction and fixation of aromas on a non-aqueous substrate, wherein aromatic plants and a non-aqueous solvent selected from a fat or oil are disposed in a treatment zone and microwave radiation is produced in the treatment zone so as to heat primarily the aqueous parts of the plants rather than the components of the substrate, said apparatus comprising:

(i) a control circuit which enables regulation of the radiation exposure as a function of the temperature measured by a sensor or a period of radiation exposure measured by a timer, with the control circuit regulating the apparatus as a function of a predetermined algorithm;

(ii) a treatment vessel having a treatment zone therein which is bounded by at least one wall impermeable to microwaves and one wall transparent to microwaves, said treatment zone being produced between a metallic outer wall of the vessel and a cylindrical tube made of a material transparent to microwaves, such as plastic material;

the top part of the treatment vessel being closed by a first cover penetrated by a bore through which the top of the tube passes, it in turn closed by a second cover, with the covers being installed in a leakproof manner with seals, said first cover having attachment means made of anchoring rims and hinged latches;

the top part of the treatment zone being closed by a screen attached by tabs to the first cover, with the screen serving to isolate the treatment zone of the microwave radiation, and to push the submerged plants into the oil and to ensure a safety space;

the treatment vessel further comprising a rod attached to the shaft of the rotor of an electric motor attached to a cover, which bears a plurality of microwave emitters which are attached to an attachment means and connected electrically by lines picked up on a disk with tracks electrically supplied by brushes connected to an electric power source, said cover comprising means of forced ventilation through the tube emitters or the walls of the tube;

(iii) a means of cooling the top part of the treatment vessel by circulation or by spraying;

(iv) a means of detection of the appearance of bubbles made up of a pressure measuring units or of a means of detection of acoustic emissions or of a means of reduction of overpressures; and (v) a means of separation into which the contents of the treatment vessel are emptied after radiation, and which includes a valve for evacuation of inert materials to a waste filtering unit and of the aromatized substrate to a clarification unit.

* * * * *